United States Patent [19]

Raddatz et al.

[11] Patent Number: 4,755,592

[45] Date of Patent: Jul. 5, 1988

[54] STATINE-CONTAINING PEPTIDES USEFUL IN MEDICAMENTS

[75] Inventors: Peter Raddatz, Darmstadt; Günter Hölzemann, Seeheim; Alfred Jonczyk, Darmstadt; Claus J. Schmitges, Gross-Umstadt; Klaus-Otto Minck, Ober-Ramstadt; Hans-Eckart Radunz, Mühtal; Johannes Sombroek, Darmstadt-Eberstadt, all of Fed. Rep. of Germany

[73] Assignee: Merck Patent Gesellschaft mit beschrankter Haftung, Darmstadt, Fed. Rep. of Germany

[21] Appl. No.: 847,977

[22] Filed: Apr. 3, 1986

[30] Foreign Application Priority Data

Apr. 3, 1985 [DE] Fed. Rep. of Germany ........ 3512128

[51] Int. Cl.$^4$ .............................................. A61K 37/02
[52] U.S. Cl. .................................... 530/323; 530/328; 530/329; 530/330; 530/331; 530/332
[58] Field of Search ............... 530/323, 328, 329, 330, 530/331, 332; 514/16, 17, 18, 19

[56] References Cited

U.S. PATENT DOCUMENTS

4,638,047 1/1987 Szelke et al. ........................ 530/328

FOREIGN PATENT DOCUMENTS

077028 4/1983 European Pat. Off. .

Primary Examiner—Delbert R. Phillips
Assistant Examiner—Nathan M. Nutter
Attorney, Agent, or Firm—Millen & White

[57] ABSTRACT

New peptides of the formula I $$X-Z-W-E-W'-Y \qquad \text{I}$$

wherein X, Z, W, E, W' and Y are as defined herein and their salts inhibit the activity of human plasma renin.

24 Claims, No Drawings

STATINE-CONTAINING PEPTIDES USEFUL IN MEDICAMENTS

BACKGROUND OF THE INVENTION

This invention relates to new peptides.

Similar compounds are known from European Patent No. A-77,028.

SUMMARY OF THE INVENTION

It is an object of this invention to provide new compounds with useful properties, in particular those which can be used for the preparation of medicaments.

Upon further study of the specification and appended claims, further objects and advantages of this invention will become apparent to those skilled in the art.

These objects have been achieved by providing new peptides of the formula I

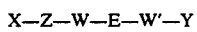   I wherein

X is H, $R^1$—O—$C_mH_{2m}$—CO—, $R^1$—$C_mH_{2m}$—O—CO—, $R^1$—$C_mH_{2m}$—CO—, $R^1$—$SO_2$—, ($R^1$—$C_mH_{2m}$)—L($R^1$—$C_pH_{2p}$)—$C_rH_{2r}$—CO—, H—(NHCH$_2$CH$_2$)$_m$—NH—CH$_2$CO— or 9-fluorenyl-$C_mH_{2m}$—O—CO, Z is 0 to 4 amino acid radicals bonded together in peptide form and chosen independently from Abu, Ada, Ala, Arg, Asn, Bia, Dab, Gln, Gly, His, N(im)-alkyl-His, Ile, Leu, tert.-Leu, Lys, Met, Nbg, Nle, Orn, Phe, Pro, Ser, Thr, Tic, Trp, Tyr and Val, W and W' are each —$NR^2$—$CHR^3$—CH-$R^4$—(CHR$^5$)$_n$—CO—, independently, E is 0 to 2 amino acid radicals bonded to one another in peptide form and chosen independently from Abu, Ala, Ile, Leu, Met, Nle and Val, Y is —O—$C_tH_{2t}$—$R^6$, —NH—$C_tH_{2t}$—$R^6$ or $NA_2$, or W'—Y is also

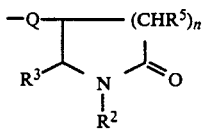

$R^1$ and $R^3$ are each A, Ar, Ar-alkyl, cycloalkyl which has 3–7C atoms and is unsubstituted or mono- or polysubstituted by alkyl, alkoxy and/or Hal, cycloalkylalkyl with 4–11C atoms, bicycloalkyl or tricycloalkyl with in each case 7–14C atoms or bicycloalkyl-alkyl or tricycloalkyl-alkyl with in each case 8–18C atoms, independently, $R^2$, $R^5$ and $R^6$ are each H or A, independently, $R^4$ is OH or NH$_2$, L is CH or N, m, p, r and t are each 0, 1, 2, 3, 4 or 5, independently n is 1 or 2, Q is O or NH, Ar is phenyl which is unsubstituted or mono- or polysubstituted by A, AO, Hal, CF$_3$, OH and/or NH$_2$, or is unsubstituted naphthyl, Hal is F, Cl, Br or I and A is alkyl with 1–8C atoms, and wherein, furthermore, one or more —NH—CO— groups can also be replaced by one or more —N(alkyl)—CO— groups, and wherein in W and W', one radical $R^4$ is OH and the other is NH$_2$, while the radicals $R^2$, $R^3$, $R^5$, A and Hal and the parameters n can be identical or different, and salts thereof.

DETAILED DISCUSSION

It has been found that the compounds of the formula I and their salts have very useful properties. Above all, they inhibit the activity of human plasma renin. This effect can be demonstrated, for example, by the method of F. Fyhrquist et al., Clin.Chem. 22, 250–256 (1976). It is remarkable that these compounds are very specific inhibitors of renin; considerably higher concentrations of these compounds are necessary for inhibition of other aspartyl-proteinases (for example pepsin and cathepsin D), concentrations about 100 to 10 000 times as high.

The compounds can be used as medicament active compounds in human and veterinary medicine, in particular for the prophylaxis and treatment of cardiac, circulatory and vascular diseases, above all hypertension, cardiac insufficiency and hyperaldosteronism. The compounds can also be used for diagnostic purposes in order to determine the possible contribution of the renin activity in maintaining the pathological state in patients with hypertension or hyperaldosteronism.

The abbreviations of amino acid radicals given above and below represent the radicals —NH—CHR—CO— (wherein R has the specific meaning known for each amino acid) of the following amino acids:

Abu: 2-aminobutyric acid
Ada: adamantylalanine
Ala: alanine
Arg: arginine
Asn: asparagine
Bia: benzimidazolylalanine
Dab: 2,4-diaminobutyric acid
Gln: glutamine
Gly: glycine
His: histidine
N(im)-alkyl-His: histidine substituted by A in the 1- or 3-position of the imidazole ring
Ile: isoleucine
Leu: leucine
tert.-Leu: tert.-leucine
Lys: lysine
Met: methionine
Nbg: (2-norbornyl)-glycine
Nle: norleucine
N-Me-His: N-methyl-histidine
N-Me-Phe: N-methyl-phenylalanine
Orn: ornithine
Phe: phenylalanine
Pro: proline
Ser: serine
Thr: threonine
Tic: tetrahydroisoquinoline-1-carboxylic acid
Trp: tryptophan
Tyr: tyrosine
Val: valine Furthermore, the symbols below have the following meanings:

BOC: tert.-butoxycarbonyl
imi-BOM: benzyloxymethyl in the 1-position of the imidazole ring
CBZ: benzyloxycarbonyl
DNP: 2,4-dinitrophenyl
FMOC: 9-fluorenylmethoxycarbonyl
imi-DNP: 2,4-dinitrophenyl in the 1-position of the imidazole ring OMe: methyl ester
POA: phenoxyacetyl
DCCI: dicyclohexylcarbodiimide
HOBt: 1-hydroxybenzotriazole.

Where the abovementioned amino acids can occur in several enantiomeric forms, all of these forms and also their mixtures (for example the DL forms) are included above and below, for example as a constituent of the compounds of the formula I. The L-forms are preferred. Where individual compounds are mentioned below, the abbreviations of these amino acids in each case relate to the L-form, unless expressly indicated otherwise.

The radicals and parameters X, Z, W, E, W', Y, $R^1$ to $R^6$, L, m, n, p, r, t, Q, Ar, Hal and A above and below have the meanings given in the case of formula I, unless expressly indicated otherwise.

In the above formulae, A has 1–8, preferably 1, 2, 3 or 4, C atoms. A is preferably methyl, ethyl, propyl, isopropyl, butyl, isobutyl, sec.-butyl or tert.-butyl, or furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl or 1,1,2- or 1,2,2-trimethylpropyl.

Cycloalkyl is preferably cyclopropyl, cyclobutyl, cyclopentyl, cyclohexyl or cycloheptyl, but also, for example, 1-, 2- or 3-methylcyclopentyl or 1-, 2-, 3- or 4-methylcyclohexyl.

Cycloalkyl-alkyl accordingly is preferably cyclopropylmethyl, 2-cyclopropylethyl, cyclobutylmethyl, 2-cyclobutylethyl, cyclopentylmethyl, 2-cyclopentylethyl, cyclohexylmethyl or 2-cyclohexylethyl, but also, for example, 1-, 2- or 3-methylcyclopentylmethyl or 1-, 2-, 3- or 4-methylcyclohexylmethyl.

Bicycloalkyl is preferably 1- or 2-decalyl, 2-bicyclo[2,2,1]heptyl or 6,6-dimethyl-2-bicyclo[3,1,1]-heptyl.

Tricycloalkyl is preferably 2-adamantyl.

Ar is preferably phenyl, or furthermore o-, m- or p-tolyl, o-, m- or p-ethylphenyl, o-, m- or p-methoxyphenyl, o-, m- or p-fluorophenyl, o-, m- or p-chlorophenyl, o-, m- or p-bromophenyl, o-, m- or p-iodophenyl, o-, m- or p-trifluoromethylphenyl, 2,3-, 2,4-, 2,5-, 2,6-, 3,4- or 3,5-dimethoxyphenyl, 3,4,5-trimethoxyphenyl, o-, m- or p-aminophenyl or 1- or 2-naphthyl.

$R^1$ is preferably A, in particular methyl, ethyl, propyl, isopropyl, butyl, isobutyl or tert.-butyl, or furthermore preferably cyclopropyl, cyclopentyl, cyclohexyl, phenyl or benzyl.

$R^2$, $R^5$ and $R^6$ are preferably H or methyl, or furthermore ethyl, propyl, isopropyl, butyl or isobutyl.

$R^3$ is perferably A, in particular methyl, ethyl, propyl, isopropyl, isobutyl, sec.-butyl, pentyl, isopentyl (3-methylbutyl) or 2-methylbutyl; cyclohexylmethyl or 2-cyclohexylethyl; or benzyl, p-chlorobenzyl; bicyclo[2,2,1]heptyl-2-methyl or 6,6-dimethylbicyclo[3,1,1]-heptyl-2-methyl. Particularly preferred radicals $R^3$ are isobutyl, benzyl and cyclohexylmethyl.

m, p, r and t are preferably 0, 1 or 2; n is preferably 1.

X is preferably H, POA, alkoxycarbonyl, such as BOC, CBZ, alkanoyl, such as acetyl, propionyl, butyryl or isobutyryl, cycloalkylcarbonyl, such as cyclopentylcarbonyl or cyclohexylcarbonyl, aroyl, such as benzoyl, arylalkanoyl, such as phenylacetyl, 2- or 3-phenylpropionyl, 4-phenylbutyryl, 2-benzyl-4-phenylbutyryl, 2- or 3-o-, -m- or -p-fluorophenylpropionyl, 2- or 3-o-, -m- or -p-chlorophenylpropionyl or cycloalkylalkanoyl, such as cyclohexylacetyl or 2- or 3-cyclohexylpropionyl. Particularly preferred radicals X are H, BOC, CBZ, 4-phenylbutyryl and 2-benzyl-4-phenylbutyryl.

Z is 0 (=valence bond) or 1, preferably 2, 3 or 4 amino acid radicals bonded to one another in peptide form, in particular the groups His, Phe-His, Pro-Phe-His or His-Pro-Phe-His, and furthermore preferably the groups Abu, Ada, Asn, Bia, Gln, N-(im)-alkyl-His, Leu, Nle, Phe, Trp, Tyr, Abu-His, Ada-His, Ala-His, Ala-Phe, Arg-His, Asn-His, Bia-His, Dab-His, Gly-His, His-His, Ile-His, Leu-His, tert.-Leu-His, Lys-His, Met-His, Nbg-His, Nle-His, (N-Me-His)-His, (N-Me-Phe)-His, Orn-His, Phe-Abu, Phe-Ada, Phe-Ala, Phe-Arg, Phe-Asn, Phe-Bia, Phe-Dab, Phe-Gln, Phe-Gly, Phe-(N-im-alkyl-His), Phe-Ile, Phe-Leu, Phe-tert.-Leu, Phe-Lys, Phe-Met, Phe-Nbg, Phe-Nle, Phe-(N-Me-His), Phe-(N-Me-Phe), Phe-Orn, Phe-Phe, Phe-Pro, Phe-Ser, Phe-Thr, Phe-Tic, Phe-Trp, Phe-Tyr, Phe-Val, Pro-His, Ser-His, Thr-His, Tic-His, Trp-His, Tyr-His, Val-His, Ada-Phe-His, Pro-Ala-His, Pro-Ala-Phe, Pro-Phe-Ala, Pro-Phe-Phe, His-Pro-Ala-His, His-Pro-Ala-Phe, His-Pro-Phe-Ala, His-Pro-Phe-Phe, furthermore Pro-Abu-His, Pro-Ada-His, Pro-Arg-His, Pro-Asn-His, Pro-Bia-His, Pro-Dab-His, Pro-Gly-His, Pro-His-His, Pro-Ile-His, Pro-Leu-His, Pro-tert.-Leu-His, Pro-Lys-His, Pro-Met-His, Pro-Nbg-His, Pro-Nle-His, Pro-(N-Me-His)-His, Pro-(N-Me-Phe)-His, Pro-Orn-His, Pro-Phe-Abu, Pro-Phe-Ada, Pro-Phe-Arg, Pro-Phe-Asn, Pro-Phe-Bia, Pro-Phe-Dab, Pro-Phe-Gln, Pro-Phe-Gly, Pro-Phe-(N-im-alkyl-His), Pro-Phe-Ile, Pro-Phe-Leu, Pro-Phe-tert.-Leu, Pro-Phe-Lys, Pro-Phe-Met, Pro-Phe-Nbg, Pro-Phe-Nle, Pro-Phe-(N-Me-His), Pro-Phe-(N-Me-Phe), Pro-Phe-Orn, Pro-Phe-Pro, Pro-Phe-Ser, Pro-Phe-Thr, Pro-Phe-Tic, Pro-Phe-Trp, Pro-Phe-Tyr, Pro-Phe-Val, Pro-Pro-His, Pro-Ser-His, Pro-Thr-His, Pro-Tic-His, Pro-Trp-His, Pro-Tyr-His, Pro-Val-His, His-Pro-Abu-His, His-Pro-Ada-His, His-Pro-Arg-His, His-Pro-Asn-His, His-Pro-Bia-His, His-Pro-Dab-His, His-Pro-Gly-His, His-Pro-His-His, His-Pro-Ile-His, His-Pro-Leu-His, His-Pro-tert.-Leu-His, His-Pro-Lys-His, His-Pro-Met-His, His-Pro-Nbg-His, His-Pro-Nle-His, His-Pro-(N-Me-His)-His, His-Pro-(N-Me-Phe)-His, His-Pro-Orn-His, His-Pro-Phe-Abu, His-Pro-Phe-Ada, His-Pro-Phe-Arg, His-Pro-Phe-Asn, His-Pro-Phe-Bia, His-Pro-Phe-Dab, His-Pro-Phe-Gln, His-Pro-Phe-Gly, His-Pro-Phe(N-im-alkyl-His), His-Pro-Phe-Ile, His-Pro-Phe-Leu, His-Pro-Phe-tert.-Leu, His-Pro-Phe-Lys, His-Pro-Phe-Met, His-PrO-Phe-Nbg, His-Pro-Phe-Nle, His-Pro-Phe-(N-Me-His), His-Pro-Phe-(N-Me-Phe), His-Pro-Phe-Orn, His-Pro-Phe-Pro, His-Pro-Phe-Ser, His-Pro-Phe-Thr, His-Pro-Phe-Tic, His-Pro-Phe-Trp, His-Pro-Phe-Tyr, His-Pro-Phe-Val, His-Pro-Pro-His, His-Pro-Ser-His, His-Pro-Thr-His, His-Pro-Tic-His, His-Pro-Trp-His, His-Pro-Tyr-His or His-Pro-Val-His.

E is preferably absent or is preferably Ile, or furthermore preferably Leu, and furthermore Abu, Ala, Met, Nle or Val.

One of the groups W and W' is —$NR^2$—$CHR^3$—CHOH—$(CHR^5)_n$—CO—, preferably —NH—CH$R^3$—CHOH—$CH_2$—CO—, in particular —NH—CH-(isobutyl)—CHOH—$CH_2$—CO— ("Sta"; derived from statine), —NH—CH(benzyl)—CHOH—$CH_2$—CO— ("AHPP"; derived from 4-amino-3-hydroxy-5-phenylpentanoic acid), —NH—CH(cyclohexylmethyl)—CHOH—$CH_2$—CO— ("AHCP", derived from 4-amino-3-hydroxy-5-cyclohexylpentanoic acid) or —NH—CH($CH_2CH_2$-cyclohexyl)—CHOH—$CH_2$—CO— ("AHCH"; derived from 4-amino-3-hydroxy-6- cyclohexyl-hexanoic acid), and the other of the groups W and W' is —NR²—CHR³—CH(NH₂)—(CHR⁵-)ₙ—CO, preferably —NH—CHR³—CH(NH₂)—CH₂—CO—, in particular —NH—CH(isobutyl)—CH(NH₂)—CH₂—CO— ("DAMH"; derived from 3,4-diamino-6-methylheptanoic acid), —NH—CH(benzyl)—CH(NH₂)—CH₂—CO— ("DAPP"; derived from 3,4-diamino-5-phenylpentanoic acid), —NH—CH(cyclohexylmethyl)—CH(NH₂)—CH₂—CO— ("DACP"; derived from 3,4-diamino-5-cyclohexylpentanoic acid) or —NH—CH(CH₂CH₂-cyclohexyl)—CH(NH₂)—CH₂—CO— ("DACH"; derived from 3,4-diamino-6-cyclohexyl-hexanoic acid).

The groups W and W' have at least two chiral centers. They can therefore occur in various—optically inactive or optically active—forms. Formula I includes all these forms. If W and/or W' is —NH—CHR³—CHR⁴—CH₂—CO—, the 3S-hydroxy-4S-amino enantiomers or the 3S,4S-diamino enantiomers are preferred. Unless indicated otherwise in the designation of individual substances, the abbreviations Sta, AHPP, AHCP, AHCH, DAMH, DAPP, DACP and DACH always relate to these 3S,4S-forms.

Y is preferably OR⁶, in particular OA, or —NH—C$_t$H$_{2t}$—R⁶, wherein the group C$_t$H$_{2t}$ is preferably straight-chain alkylene with 1-5 C atoms, in particular —CH₂—, —CH₂CH₂— or —(CH₂)₃—, or furthermore also —(CH₂)₄— or —(CH₂)₅—, but also, for example, —CH(CH₃)—, —CH(CH₃)—CH₂— or —CH₂—CH(CH₃)—. A preferred meaning of the group —NH—C$_t$H$_{2t}$—R⁶ is also NH₂.

The preferred number of substituents in the substituted cycloalkyl and phenyl groups mentioned above is 1 to 3, more preferably 1 or 2.

The invention accordingly particularly relates to those compounds of the formula I in which at least one of the radicals mentioned has one of the abovementioned preferred meanings. Some preferred groups of compounds can be expressed by the following part formulae Ia to If, which correspond to the formula I but wherein, in Ia
X is H, POA, BOC, 4-phenylbutyryl, 2-benzyl-4-phenylbutyryl or CBZ,
Z is absent or is His, Phe-His, Pro-Phe-His or His-Pro-Phe-His,
W is (a) —NH—CHR³—CHOH—CH₂—CO— or (b) —NH—CHR³—CH(NH₂)—CH₂—CO—,
E is absent or is Ile or Leu,
W' is (a) —NH—CHR³—CH(NH₂)—CH₂—CO— or (b) —NH—CHR³—CHOH—CH₂—CO—,
R³ is isobutyl, benzyl or cyclohexylmethyl and
Y is OH or OMe, or
W'-Y is also

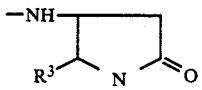

in Ib
X is H, POA, BOC, 4-phenylbutyryl, 2-benzyl-4-phenylbutyryl or CBZ,
Z is absent or is His, Phe-His, Pro-Phe-His or His-Pro-Phe-His,
W is —NH—CHR³—CHOH—CH₂—CO—,
E is absent or is Ile or Leu,
W' is —NH—CHR³—CH(NH₂)—CH₂—CO—,
R³ is isobutyl, benzyl or cyclohexylmethyl and
Y is OH or Ome;

in Ic
X is H, POA, BOC, 4-phenylbutyryl, 2-benzyl-4-phenylbutyryl or CBZ,
Z is absent or is His, Phe-His, Pro-Phe-His or His-Pro-Phe-His,
W is —NH—CHR³—CH(NH₂)—CH₂—CO—,
E is absent or is Ile or Leu,
W' is —NH—CHR³—CHOH—CH₂—CO—,
R³ is isobutyl, benzyl or cyclohexylmethyl and
Y is OH or OMe;

in Id
X is H, POA, BOC, 4-phenylbutyryl, 2-benzyl-4-phenylbutyryl or CBZ,
Z is absent or is His, Phe-His, Pro-Phe-His or His-Pro-Phe-His,
W is —NH—CHR³—CHR⁴—CH₂—CO—,
E is absent or is Ile or Leu,
W'-Y is

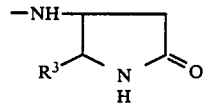

and
R³ is isobutyl, benzyl or cyclohexylmethyl;

in Ie
X is H or BOC,
Z is Phe-His,
W is (a) Sta or (b) DAMH, DACP or DAPP,
E is absent or is Ile or Leu,
W' is (a) DAMH, DACP or DAPP or (b) Sta and
Y is OH or OMe, or
W'-Y is also

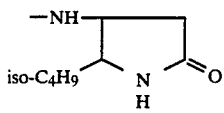

in If
X is BOC and
Z, W, E, W' and Y have the meaning given in the case of formula Ie.

The invention furthermore relates to a process for the preparation of a peptide of the formula I and of its salts, characterized in that it is liberated from one of its functional derivatives by treatment with a solvolyzing or hydrogenolyzing agent, or in that a compound which corresponds to the formula I but contains one or more additional groups which can be split hydrogenolytically and/or C—C and/or C—N and/or C—O bonds instead of H atoms is reduced, or in that an amino-keto acid derivative which corresponds to the formula I but contains a CO group instead of a CH(NH₂) group is aminated reductively, or in that a carboxylic acid of the formula II $$\text{Ti X—G¹—OH} \quad\quad \text{II}$$

wherein G¹ is
(a) Z¹,
(b) Z,
(c) Z—W or
(d) Z—W—E is reacted with an amine of the formula III

H—G²—Y    III wherein G² is
(a) Z²—W—E—W′,
(b) W—E—W′,
(c) E—W′ or
(d) W′ and

Z¹+Z² together are Z, and in that, if appropriate, a functionally modified amino and/or hydroxyl group in a compound of the formula I is liberated by treatment with solvolyzing or hydrogenolyzing agents and/or a compound of the formula I is converted into one of its salts by treatment with an acid or base.

The compounds of the formula I and also the starting substances for their preparation are moreover prepared by methods which are known per se, such as are described in the literature (for example in the standard works, such as Houben-Weyl, Methoden der Organischen Chemie (Methods of Organic Chemistry), Georg-Thieme-Verlag, Stuttgart; and furthermore European Patent No. A-45,665, European Patent No. A-77,028, European Patent No. A-77,029 and European Patent No. A-81,783), and in particular under reaction conditions which are known and suitable for the reactions mentioned. It is also possible to utilize known variants which are not mentioned in more detail here.

If desired, the starting substances can also be formed in situ, so that they are not isolated from the reaction mixture but are immediately reacted further to give the compounds of the formula I.

The compounds of the formula I are preferably obtained by liberating them from their functional derivatives by solvolysis, in particular hydrolysis, or by hydrogenolysis.

Preferred starting substances for the solvolysis or hydrogenolysis are those which contain corresponding protected amino and/or hydroxyl groups instead of one or more free amino and/or hydroxyl groups, preferably those which carry an amino-protective group instead of an H atom bonded to an N atom, in particular those of the formula IV

X—Z—W¹—E—W²—Y    IV wherein one of the radicals W¹ and W² is —NR²—CHR³—CH(NHR⁷)—(CHR⁵)ₙ—CO—, the other of these radicals is —NR²—CHR³—CHOH—(CHR⁵)ₙ—CO— and R⁷ is an amino-protective group, and W²—Y is also

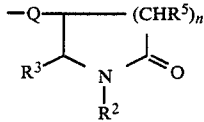

Starting substances which carry a hydroxyl-protective group instead of the H atom of a hydroxyl group are furthermore preferred.

It is also possible for several—identical or different—protected amino and/or hydroxyl groups to be present in the molecule of the starting substance. If the protective groups present differ from one another, they can in many cases be split off selectively.

The expression "amino-protective group" is generally known and relates to groups which are suitable for protecting (blocking) an amino group from chemical reactions, but which can easily be removed when the desired chemical reaction elsewhere in the molecule has been carried out. Typical examples of such groups are, in particular, unsubstituted or substituted acyl groups, and furthermore unsubstituted or substituted aryl (for example 2,4-dinitrophenyl) or aralkyl groups (for example benzyl, 4-nitrobenzyl or triphenylmethyl). Since the amino-protective groups are removed after the desired reaction (or reaction sequence), their nature and size is otherwise not critical; however, those with 1-20, in particular 1-8, C atoms are preferred. The expression "acyl group" in connection with the present process is to be interpreted in the broadest sense. It includes acyl groups derived from aliphatic, araliphatic, aromatic or heterocyclic carboxylic acids or sulfonic acids and, in particular, alkoxycarbonyl, aryloxycarbonyl and, above all, aralkoxycarbonyl groups. Examples of such acyl groups are alkanoyl, such as acetyl, propionyl and butyryl; aralkanoyl, such as phenylacetyl; aroyl, such as benzoyl or toluyl; aryloxyalkanoyl, such as phenoxyacetyl; alkoxycarbonyl, such as methoxycarbonyl, ethoxycarbonyl, 2,2,2-trichloroethoxycarbonyl, BOC and 2-iodoethoxycarbonyl; aralkyloxycarbonyl, such as CBZ ("carbobenzoxy"), 4-methoxybenzyloxycarbonyl and FMOC. Preferred amino-protective groups are CBZ, FMOC, benzyl and acetyl.

The expression "hydroxyl-protective group" is likewise generally known and relates to groups which are suitable for protecting a hydroxyl group from chemical reactions but can easily be removed after the desired chemical reaction at other points in the molecule has been carried out. Typical examples of such groups are the abovementioned unsubstituted or substituted aryl, aralkyl or acyl groups, and furthermore also alkyl groups. The nature and size of the hydroxyl-protective groups is not critical, since they are removed again after the desired chemical reaction or the reaction sequence; groups with 1-20, in particular 1-10, C atoms are preferred. Examples of hydroxyl-protective groups are, inter alia, benzyl, p-nitrobenzoyl, p-toluenesulfonyl and acetyl, benzyl and acetyl being particularly preferred.

The hydroxyl group can also be part of a carboxyl group, so that a carboxyl-protective group is used as the hydroxyl-protective group. The carboxyl group can thus be bonded to a polymer in accordance with the principle of the "Merrifield" synthesis, for example in ester form.

The functional derivatives of the compounds of the formula I to be used as starting substances can be prepared by customary methods of amino acid and peptide synthesis, such as are described, for example, in the standard works and patent applications mentioned.

The liberation of the compounds of the formula I from their functional derivatives is effected—depending on the protective group used—with, for example, strong acids, advantageously with trifluoroacetic acid or perchloric acid, but also with other strong inorganic acids, such as hydrochloric acid or sulfuric acid, strong organic carboxylic acids, such as trichloroacetic acid, or sulfonic acids, such as benzene- or p-toluene-sulfonic acid. It is possible but not always necessary for an additional inert solvent to be present. Preferred suitable inert solvents are organic, for example carboxylic, acids, such as acetic acid, ethers, such as tetrahydrofuran or dioxane, amides, such as dimethylformamide (DMF), halogenated hydrocarbons, such as methylene chloride, and furthermore also alcohols, such as methanol, ethanol or isopropanol, as well as water. Mixtures of the abovementioned solvents are furthermore possible. Trifluoroacetic acid is preferably used in excess, without addition of a further solvent, and perchloric acid is used in the form of a mixture of acetic acid and 70% perchloric acid in a ratio of 9:1. The reaction temperatures for the splitting are advantageously between about 0° and about 50°, and the reaction is preferably carried out between 15° and 30° (room temperature).

The BOC group can preferably be split off, for example, with 40% trifluoroacetic acid in methylene chloride or with about 3 to 5N HCl in dioxane at 15°-30°, and the FMOC group can preferably be split off with an approximately 5 to 20% solution of dimethylamine, diethylamine or piperidine in DMF at 15°-30°. The DNP group is also split off, for example, with an approximately 3 to 10% solution of 2-mercaptoethanol in DMF/water at 15°-30°. According to the "Merrifield" method, compounds of the formula I (Y=OH) are advantageously split off from the polymeric carrier with trifluoroacetic acid.

Protective groups which can be removed hydrogenolytically (for example CBZ or benzyl) can be split off, for example, by treatment with hydrogen in the presence of a catalyst (for example a noble metal catalyst, such as palladium, advantageously on a support, such as charcoal). Suitable solvents here are those mentioned above, in particular, for example, alcohols, such as methanol or ethanol, or amides, such as DMF. The hydrogenolysis is as a rule carried out at temperatures between about 0° and 100° under pressures between about 1 and 200 bar, preferably at 20°-30° under 1-10 bar. Hydrogenolysis of the CBZ group is easily effected, for example, on 5 to 10% Pd-C in methanol at 20°-30°.

The compounds of the formula I can also be obtained by reduction of corresponding compounds which, instead of H atoms, contain one or more additional groups which can be split off hydrogenolytically and/or C—C and/or C—N and/or C—O bonds.

Thus, for example, keto compounds of the formulae

X—Z—NR$^2$—CHR$^3$—CO—(CHR$^5$)$_n$—CO—E—NR$^2$—CHR$^3$—CH(NH$_2$)—(CHR$^{5\text{-}}$)$_n$—CO—Y  (V)

or

X—Z—NR$^2$—CHR$^3$—CH(NH$_2$)—(CHR$^{5\text{-}}$)$_n$—CO—E—NR$^2$—CHR$^3$—CO—(CHR$^5$)$_n$—Y  (VI)

can be reduced to compounds of the formula I, for example with a complex metal hydride, such as NaBH$_4$, which does not simultaneously reduce the peptide-carbonyl groups, in an inert solvent, such as methanol, at temperatures between about −10° and +30°.

The compounds of the formulae V and VI can be obtained, for example, by reaction of an amino acid of the formula X—Z—NR$^2$—CHR$^3$—COOH or X—Z—NR$^2$—CHR$^3$—CH(NH$_2$)—(CHR$^5$)$_n$—CO—E—NR$^2$—CHR$^3$—COOH with carbonyldiimidazole to give the corresponding imidazolide and subsequent reaction with malonic acid derivatives of the formulae HOOC—CH$_2$—CO—E—NR$^2$—CHR$^3$—CH(NH$_2$)—(CHR$^5$)$_n$—CO—Y or esters or salts thereof, and subsequent decarboxylation.

The compounds of the formula I can also be prepared by reductive amination of amino-keto acid derivatives of the formulae V or VI.

The reductive amination can be carried out in one or several stages. Thus, it is possible to treat the compound V or VI with ammonium salts, for example ammonium acetate, and NaCNBH$_3$, preferably in an inert solvent, for example an alcohol, such as methanol, at temperatures between about 0° and 50°, in particular between 15° and 30°.

It is furthermore possible for the ketone V or VI first to be converted into the oxime with hydroxylamine in the customary manner and to reduce this to the amine, for example by catalytic hydrogenation on Raney nickel.

Compounds of the formula I, in particular those in which W is —NR$^2$—CHR$^3$—CHOH—(CHR$^{5\text{-}}$)$_n$—CO— and W'—Y is

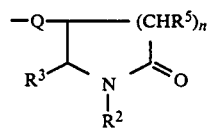

can also be obtained by direct peptide synthesis from a carboxylic acid and an amino component. Suitable carboxylic acid components are, for example, those of the part formulae X—Z—OH, X—Z—W—OH or X—Z—W—E—OH, and suitable amino components are those of the part formulae H—W—E—W'—Y, H—E—W'—Y or H—W'—Y. The peptide bond can, however, also be linked within the group Z; a carboxylic acid of the formula X—Z$^1$—OH is here reacted with an amino-peptide of the formula H—Z$^2$—W—E—W'—Y, wherein Z$^1$+Z$^2$=Z. The reaction is advantageously carried out by the customary methods of peptide synthesis, such as are described, for example, in Houben-Weyl, loc.cit., volume 15/II, pages 1 to 806 (1974).

The reaction is preferably effected in the presence of a dehydrating agent, for example a carbodiimide, such as DCCI or dimethylaminopropylethyl-carbodiimide, and furthermore propanephosphonic anhydride (compare Angew. Chem. 92, 129 (1980)), diphenylphosphoryl azide or 2-ethoxy-N-ethoxycarbonyl-1,2-dihydroquinoline, in an inert solvent, for example a halogenated hydrocarbon, such as methylene chloride, an ether, such as tetrahydrofuran or dioxane, an amide, such as dimethylformamide (DMF) or dimethylacetamide, or a nitrile, such as acetonitrile, at temperatures between about −10 and 40, preferably between 0° and 30°.

Instead of II or III, it is also possible to use suitable reactive derivatives of these substances in the reaction, for example those in which reactive groups are intermediately blocked by protective groups. The amino acid derivatives III can be used, for example, in the form of their activated esters, which are advantageously formed in situ, for example by addition of 1-hydroxybenzotriazole or N-hydroxysuccinimide.

The starting substances of the formula II and III are known in most cases. Where they are not known, they can be prepared by known methods, for example the abovementioned methods of peptide synthesis and splitting off of protective groups.

If desired, a functionally modified amino and/or hydroxyl group in a compound of the formula I can be liberated by solvolysis or hydrogenolysis by one of the methods described above.

Thus, in particular, a compound of the formula I wherein X is other than H can be converted into a compound of the formula I (X=H), advantageously by hydrogenolysis, if X is CBZ, and otherwise by selective solvolysis. If X is BOC, the BOC group can be split off, for example, with HCl in dioxane at room temperature.

It is furthermore possible, for example, to hydrolyze an ester of the formula I (Y=—O—$C_rH_{2r}$—A) to the corresponding acid of the formula I (Y=OH), for example with aqueous-dioxanic sodium hydroxide solution at room temperature.

A base of the formula I can be converted into the associated acid addition salt with an acid. Possible acids for this reaction are, in particular, those which give physiologically acceptable salts. Thus, inorganic acids can be used, for example sulfuric acid, nitric acid, hydrogen halide acids, such as hydrochloric acid or hydrobromic acid, phosphoric acids, such as orthophosphoric acid, and sulfamic acid, and furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -di-sulfonic acids and laurylsulfuric acid. Salts with physiologically unacceptable acids, for example picrates, can be used to isolate and/or purify the compounds of the formula I.

An acid of the formula I can be converted into one of its physiologically acceptable metal or ammonium salts by reaction with a base. Possible salts are, in particular, the sodium, potassium, magnesium, calcium and ammonium salts, and furthermore substituted ammonium salts, for example the dimethyl-, diethyl- or diisopropylammonium, monoethanol-, diethanol- and triethanolammonium, cyclohexylammonium, dicyclohexylammonium and dibenzylethylenediammonium salts, and furthermore, for example, salts with N-methyl-D-glucamine or with basic amino acids, such as arginine or lysine.

The new active compounds of the formula 1 and their physiologically acceptable salts can be used for the preparation of pharmaceutical products by bringing them into a suitable dosage form together with at least one excipient or auxiliary and, if desired, together with one or more other active compound(s). The formulations thus obtained can be used as medicaments in human or veterinary medicine. Possible carrier substances are organic or inorganic substances which are suitable for enteral (for example rectal) or parenteral administration or for administration in the form of an inhalation spray and with which the new compounds do not react, for example water, vegetable oils, benzyl alcohols, polyethylene glycols, glycerol triacetate and other fatty acid glycerides, gelatine and soya lecithin. Suppositories are used for rectal administration and solutions, preferably oily or aqueous solutions, and furthermore suspensions, emulsions or implants are used for parenteral administration. Sprays which contain the active compound either dissolved or suspended in a propellant gas mixture (for example fluoro-chlorohydrocarbons) can be used for administration of an inhalation spray. The active compound is thereby advantageously used in micronized form, it being possible for one or more additional physiologically acceptable solvents to be present, for example ethanol. Inhalation solutions can be administered with the aid of customary inhalers. The new compounds can also be lyophilized and the resulting lyophilizates can be used, for example, for the preparation of injection products. The formulations mentioned can be sterilized and/or can contain auxiliaries, such as preservatives, stabilizers and/or wetting agents, emulsifiers, salts for influencing the osmotic pressure, buffer substances and colorants and/or aroma substances. If desired, they can also contain one or more other active compounds, for example one or more vitamins.

The substances according to the invention are as a rule administered analogously to other known commercially available peptides, but in particular analogously to the compounds described in European Patent No. A-77,028, preferably in dosages between about 100 mg and 30 g, in particular between 500 mg and 5 g, per dosage unit. The daily dosage is preferably between about 2 and 600 mg/kg of body weight. The specific dose for each particular patient depends, however, on the most diverse factors, for example on the activity of the particular compound employed, on age, weight, general state of health and sex, on the diet, on the time and route of administration and on the rate of excretion, medicament combination and severity of the particular disease to which the therapy applies. Parenteral administration is preferred.

Renin-associated hypertension and hyperaldosteronism are effectively treated by administration of from 10 to 300 mg/kg of body weight. For diagnostic purposes, the novel peptides may be administered in a single dose of from 0.1 to 10 mg/kg of body weight.

In the following examples, "customary working up" means: water is added, if necessary, the mixture is extracted with ether or methylene chloride, the phases are separated, the organic phase is dried over sodium sulfate, filtered and evaporated and the residue is purified by chromatography on silica gel and/or crystallization.

EXAMPLE 1

1.2 g of N-(3S-FMOC-amino-4S-BOC-L-phenylalanyl-L-histidyl-amino-6-methyl-heptanoyl-L-isoleucyl)-statine methyl ester ["BOC-Phe-His-(3-FMOC)-DAMH-Ile-Sta-OMe"; obtainable by reaction of methyl 3-oxo-4S-BOC-amino-6-methylheptanoate with ammonium acetate/NaCNBH$_3$/methanol to give methyl 3S-amino-4S-BOC-amino-6-methylheptanoate (m.p. 80°; in addition the 3R-epimer, m.p. 97°), hydrolysis to 3S-amino-4S-BOC-amino-6-methyl-heptanoic acid ("BOC-DAMH"; m.p. 221°–222°), reaction with FMOC chloride to give 3S-FMOC-amino-4S-BOC-amino-6-methyl-heptanoic acid (m.p. 115°–117°), reaction with Ile-(3R,4S)-Sta-OMe/DCCI/HOBt to give 3S-FMOC-amino-4S-BOC-amino-6-methylheptanoyl-Ile-(3R,4S)-Sta-OME, hydrolysis with 4N HCl/dioxane to give 3S-FMOC-amino-4S-amino-6-methylheptanoyl-Ile-(3R,4S)-Sta-OMe, reaction with BOC-(imi-DNP)-His-OH/DCCI/HOBt to give 3S-FMOC-amino-4S-BOC-(imi-DNP)-His-amino-6-methylheptanoyl-Ile-(3R,4S)-Sta-OMe, hydrolysis with 4N HCl/dioxane to give 3S-FMOC-amino-4S-(imi-DNP)-His-amino-6-methylheptanoyl-Ile-(3R,4S)-Sta-OMe, reaction with BOC-Phe-OH/DCCI/HOBt to give 3S-FMOC-amino-4S-BOC-Phe-(imi-DNP)-His-amino-6-methyl-heptanoyl-Ile-(3R,4S)-Sta-OMe and stirring for 2 hours with 2-mercaptoethanol in DMF/water 1:1 at pH 8] are dissolved in 50 ml of a 10% solution of dimethylamine in DMF, the solution is stirred at 20° for 30 minutes and evaporated and the residue is chromatographed on silica gel with methylene chloride/methanol/acetone to give N-(3S-amino-4S-BOC-L-phenylalanyl-L-histidylamino-6-methyl-heptanoyl-L-isoleucyl)-(3R,4S)-statine methyl ester ("BOC-Phe-His-DAMH-Ile-(3R,4S)-Sta-OMe"), m.p. 140°-142°.

The following compounds are obtained analogously by splitting the corresponding 3S-FMOC-amino derivatives:
BOC-Phe-His-DAMH-Ile-Sta-OMe
POA-His-DAMH-Ile-Sta-OMe
BOC-Pro-Phe-His-DAMH-Ile-Sta-OMe
BOC-His-Pro-Phe-His-DAMH-Ile-Sta-OMe
BOC-His-His-DAMH-Ile-Sta-OMe
BOC-Pro-His-DAMH-Ile-Sta-OMe
BOC-Trp-His-DAMH-Ile-Sta-OMe
BOC-Tyr-His-DAMH-Ile-Sta-OMe
CBZ-His-DAMH-Ile-Sta-OMe
CBZ-Phe-His-DAMH-Ile-Sta-OMe
as well as the other corresponding (3R,4S)-Sta derivatives.

EXAMPLE 2

A solution of 934 mg of oily N-(3S-benzylamino-4S-(BOC-Phe-His-NH)-6-methyl-heptanoyl)-Ile-(3R,4S)-Sta-OMe [obtainable by reaction of 4S-(BOC-Phe-His-NH)-6-methyl-2-heptenoyl-Ile-(3R,4S)-Sta-OMe with benzylamine at 0°] in 10 ml of methanol is hydrogenated on 0.5 g of palladium hydroxide-on-charcoal at 20° under 1 bar until the uptake of $H_2$ has ended. The catalyst is filtered off and the filtrate is evaporated to give BOC-Phe-His-DAMH-Ile-(3R,4S)-Sta-OMe, m.p. 140°-142°.

EXAMPLE 3

1 g of methyl 3R-CBZ-amino-4S-[BOC-Phe-(imi-BOM-His)-Sta-Leu-amino]-5-phenylpentanoate ["BOC-Phe-(imi-BOM-His)-Sta-Leu-(3R-CBZ-DAPP)-OMe"; obtainable by reaction of BOC-DAPP-OMe with benzyloxycarbonyl chloride to give methyl 3R-CBZ-amino-4S-BOC-amino-5-phenylpentanoate (m.p. 111°-112°), hydrolysis to give methyl 3R-CBZ-amino-4S-amino-5-phenylpentanoate ("3R-CBZ-DAPP-OMe"), reaction with BOC-Leu-OH to give methyl 3R-CBZ-amino-4S-BOC-Leu-amino-5-phenylpentanoate, splitting off the BOC group with HCl/dioxane and reaction with BOC-Phe-(imi-BOM-His)-Sta-OH/DCCI/HOBt] is dissolved in 10 ml of methanol, the solution is hydrogenated on 0.5 g of 10% Pd-C at 20° under 1 bar for 3 hours and filtered and the filtrate is evaporated to give BOC-Phe-His-Sta-Leu-(3R,4S)-DAPP-OMe, m.p. 203°.

The following compounds are obtained by hydrogenolysis of the corresponding CBZ derivatives or 3-(CBZ-amino)-imi-BOM-His derivatives, respectively:
methyl 3S-amino-4S-(BOC)-Phe-His-Sta-Leu-NH)-5-phenylpentanoate ["BOC-Phe-His-Sta-Leu-DAPP-OMe"; obtainable via methyl 3S-CBZ-amino-4S-BOC-amino-5-phenylpentanoate (m.p. 159°-160°)]
BOC-Phe-His-DAMH-Ile-Sta-NH$_2$ [obtainable via methyl 3S-CBZ-amino-4S-BOC-amino-6-methylheptanoate (m.p. 67°-68°) and 3S-CBZ-amino-4S-BOC-amino-6-methylheptanoic acid (m.p. 118°-120°)]
3R-amino-4S-(BOC-Phe-His-NH)-6-methyl-heptanoyl-Ile-Sta-NH$_2$ [obtainable via methyl 3R-CBZ-amino-4S-BOC-amino-6-methylheptanoate (m.p. 146°-148°) and 3R-CBZ-amino-4S-BOC-amino-6-methyl-heptanoic acid]
BOC-Phe-His-DAMH-Ile-(3R,4S)-Sta-OMe, m.p. 140°-142°
BOC-Pro-Phe-His-DAMH-Ile-Sta-OMe
BOC-His-Pro-Phe-His-DAMH-Ile-Sta-NH$_2$
BOC-Phe-His-DAMH-Leu-Sta-OMe
BOC-His-Pro-Phe-His-DAMH-Leu-Sta-OMe
BOC-Phe-His-DAMH-Ile-Sta-NH$_2$
BOC-Phe-His-DAMH-Leu-Sta-NH$_2$
BOC-His-Pro-Phe-Phe-DAMH-Ile-Sta-NH$_2$
BOC-His-Pro-Phe-His-DAMH-Leu-Sta-NH$_2$
BOC-Ala-His-DAMH-Ile-Sta-OMe
BOC-Arg-His-DAMH-Ile-Sta-OMe
BOC-Gly-His-DAMH-Ile-Sta-OMe
BOC-His-His-DAMH-Ile-Sta-OMe
BOC-Ile-His-DAMH-Ile-Sta-OMe
BOC-Leu-His-DAMH-Ile-Sta-OMe
BOC-Lys-His-DAMH-Ile-Sta-OMe
BOC-Met-His-DAMH-Ile-Sta-OMe
BOC-Orn-His-DAMH-Ile-Sta-OMe
BOC-Pro-His-DAMH-Ile-Sta-OMe
BOC-Ser-His-DAMH-Ile-Sta-OMé
BOC-Thr-His-DAMH-Ile-Sta-OMe
BOC-Val-His-DAMH-Ile-Sta-OMe
BOC-Phe-His-DAMH-Ile-Sta-OMe
BOC-Phe-Phe-DAMH-Ile-Sta-OMe
BOC-Phe-Tyr-DAMH-Ile-Sta-OMe
BOC-Phe-Trp-DAMH-Ile-Sta-OMe
BOC-Phe-Lys-DAMH-Ile-Sta-OMe
BOC-Phe-Orn-DAMH-Ile-Sta-OMe
BOC-Phe-Arg-DAMH-Ile-Sta-OMe
BOC-Phe-His-DAMH-Ile-Sta-OEt
acetyl-Phe-His-DAMH-Ile-Sta-OMe
acetyl-Phe-His-DAMH-Leu-Sta-NH$_2$
acetyl-Pro-Phe-His-DAMH-Leu-Sta-NH$_2$
isobutyryl-His-Pro-Phe-His-DAMH-Ala-Sta-NH$_2$
isobutyryl-Phe-His-DAMH-Ile-Sta-OMe
isobutyryl-His-Pro-Phe-His-DAMH-Ile-Sta-NH$_2$
isovaleryl-His-Pro-Phe-His-DAMH-Ile-Sta-NH$_2$
isovaleryl-His-Pro-Phe-His-DAMH-Leu-Sta-OMe
isovaleryl-His-Pro-Phe-His-DAMH-Leu-Sta-NH$_2$
benzoyl-His-DAMH-Ile-Sta-OMe
phenylacetyl-His-DAMH-Ile-Sta-OMe
α-naphthylacetyl-His-DAMH-Ile-Sta-NH$_2$
3-phenylpropionyl-His-DAMH-Ile-Sta-OMe
3-p-tolylpropionyl-His-DAMH-Ile-Sta-OMe
3-o-methoxyphenylpropionyl-His-DAMH-Ile-Sta-OMe
3-p-methoxyphenylpropionyl-His-DAMH-Ile-Sta-OMe
3-p-fluorophenylpropionyl-His-DAMH-Ile-Sta-OMe
3-p-chlorophenylpropionyl-His-DAMH-Ile-Sta-OMe
3-p-bromophenylpropionyl-His-DAMH-Ile-Sta-OMe
3-p-iodophenylpropionyl-His-DAMH-Ile-Sta-OMe
3-m-trifluoromethylphenylpropionyl-His-DAMH-Ile-Sta-OMe
3-cyclohexylpropionyl-His-DAMH-Ile-Sta-OMe
6-cycloheptylhexanoyl-His-DAMH-Ile-Sta-OMe
POA-His-DAMH-Ile-Sta-OMe
cyclopropylcarbonyl-Phe-His-DAMH-Ile-Sta-OMe
cyclopentylcarbonyl-Phe-His-DAMH-Ile-Sta-OMe
cyclohexylcarbonyl-Phe-His-DAMH-Ile-Sta-OMe
3S-amino-4S-BOC-Phe-His-amino-pentanoyl-Ile-Sta-OMe [obtainable via methyl 3S-CBZ-amino-4S-

BOC-aminopentanoate (m.p. 140°) and 3S-CBZ-amino-4S-BOC-aminopentanoic acid (oil; Rf 0.18 on silica gel with methylene chloride/methanol (9:1)]
3R-amino-4S-BOC-Phe-His-amino-pentanoyl-Ile-Sta-OMe [obtainable via methyl 3R-CBZ-amino-4S-BOC-aminopentanoate (m.p. 138°–139°)]
phenoxyacetyl-His-DAMH-Ile-Sta-OMe
2-benzyl-3-phenylpropionyl-His-DAMH-Ile-Sta-OMe
BOC-Phe-His-(3R,4S)-DAMH-Ile-Sta-OMe
BOC-Phe-Nle-DACP-Ile-Sta-OH
BOC-Phe-His-DAMH-Sta-OMe
BOC-Phe-His-DAMH-AHPP-OMe
BOC-Phe-His-DAMH-AHCP-OMe
BOC-Phe-His-DAMH-AHCH-OMe
BOC-Phe-His-DAMH-Ile-AHPP-OMe
BOC-Phe-His-DAMH-Ile-AHCP-OMe
BOC-Phe-His-DAMH-Ile-AHCH-OMe
BOC-Phe-His-DAMH-Leu-AHPP-OMe
BOC-Phe-His-DAMH-Leu-AHCP-OMe
BOC-Phe-His-DAMH-Leu-AHCH-OMe
BOC-Phe-His-DAPP-Sta-OMe
BOC-Phe-His-DAPP-AHPP-OMe
BOC-Phe-His-DAPP-AHCP-OMe
BOC-Phe-His-DAPP-AHCH-OMe
BOC-Phe-His-DAPP-Ile-Sta-OMe
BOC-Phe-His-DAPP-Ile-AHPP-OMe
BOC-Phe-His-DAPP-Ile-AHCP-OMe
BOC-Phe-His-DAPP-Ile-AHCH-OMe
BOC-Phe-His-DAPP-Leu-Sta-OMe
BOC-Phe-His-DAPP-Leu-AHPP-OMe
BOC-Phe-His-DAPP-Leu-AHCP-OMe
BOC-Phe-His-DAPP-Leu-AHCH-OMe
BOC-Phe-His-DACP-Sta-OMe, m.p. 116°–118°
BOC-Phe-His-DACP-AHPP-OMe
BOC-Phe-His-DACP-AHCP-OMe
BOC-Phe-His-DACP-AHCH-OMe
BOC-Phe-His-DACP-(3R,4S)-Sta-OMe, m.p. 134°–135°
BOC-Phe-His-DACP-Ile-AHPP-OMe
BOC-Phe-His-DACP-Ile-AHCP-OMe
BOC-Phe-His-DACP-Ile-AHCH-OMe
BOC-Phe-His-DACP-Leu-Sta-OMe
BOC-Phe-His-DACP-Leu-AHPP-OMe
BOC-Phe-His-DACP-Leu-AHCP-OMe
BOC-Phe-His-DACP-Leu-AHCH-OMe
BOC-Phe-His-DACH-Sta-OMe
BOC-Phe-His-DACH-AHPP-OMe
BOC-Phe-His-DACH-AHCP-OMe
BOC-Phe-His-DACH-AHCH-OMe
BOC-Phe-His-DACH-Ile-Sta-OMe
BOC-Phe-His-DACH-Ile-AHPP-OMe
BOC-Phe-His-DACH-Ile-AHCP-OMe
BOC-Phe-His-DACH-Ile-AHCH-OMe
BOC-Phe-His-DACH-Leu-Sta-OMe
BOC-Phe-His-DACH-Leu-AHPP-OMe
BOC-Phe-His-DACH-Leu-AHCP-OMe
BOC-Phe-His-DACH-Leu-AHCH-OMe
BOC-Phe-His-Sta-DAMH-OMe
BOC-Phe-His-Sta-DAPP-OMe
BOC-Phe-His-Sta-DACP-OMe
BOC-Phe-His-Sta-DACH-OMe
BOC-Phe-His-Sta-Ile-DAMH-OMe, m.p. 166°–167°
BOC-Phe-His-Sta-Ile-DAPP-OMe
BOC-Phe-His-Sta-Ile-DACP-OMe
BOC-Phe-His-Sta-Ile-DACH-OMe
BOC-Phe-His-Sta-Leu-DAMH-OMe, m.p. 161°–162°
BOC-Phe-His-Sta-Leu-DACP-OMe
BOC-Phe-His-Sta-Leu-DACH-OMe
BOC-Phe-His-AHPP-DAMH-OMe
BOC-Phe-His-AHPP-DAPP-OMe
BOC-Phe-His-AHPP-DACP-OMe
BOC-Phe-His-AHPP-DACH-OMe
BOC-Phe-His-AHPP-Ile-DAMH-OMe
BOC-Phe-His-AHPP-Ile-DAPP-OMe
BOC-Phe-His-AHPP-Ile-DACP-OMe
BOC-Phe-His-AHPP-Ile-DACH-OMe
BOC-Phe-His-AHPP-Leu-DAMH-OMe
BOC-Phe-His-AHPP-Leu-DAPP-OMe
BOC-Phe-His-AHPP-Leu-DACP-OMe
BOC-Phe-His-AHPP-Leu-DACH-OMe
Boc-Phe-His-AHCP-DAMH-OMe, m.p. 120°–122°
Boc-Phe-His-AHCP-DAPP-OMe
Boc-Phe-His-AHCP-DACP-OMe
Boc-Phe-His-AHCP-DACH-OMe
Boc-Phe-His-AHCP-Ile-DAMH-OMe
Boc-Phe-His-AHCP-Ile-DAPP-OMe
Boc-Phe-His-AHCP-Ile-DACP-OMe
Boc-Phe-His-AHCP-Ile-DACH-OMe
Boc-Phe-His-AHCP-Leu-DAMH-OMe
Boc-Phe-His-AHCP-Leu-DAPP-OMe
Boc-Phe-His-AHCP-Leu-DACP-OMe
Boc-Phe-His-AHCP-Leu-DACH-OMe
Boc-Phe-His-AHCH-DAMH-OMe
Boc-Phe-His-AHCH-DAPP-OMe
Boc-Phe-His-AHCH-DACP-OMe
Boc-Phe-His-AHCH-DACH-OMe
Boc-Phe-His-AHCH-Ile-DAMH-OMe
Boc-Phe-His-AHCH-Ile-DAPP-OMe
Boc-Phe-His-AHCH-Ile-DACP-OMe
Boc-Phe-His-AHCH-Ile-DACH-OMe
Boc-Phe-His-AHCH-Leu-DAMH-OMe
Boc-Phe-His-AHCH-Leu-DAPP-OMe
Boc-Phe-His-AHCH-Leu-DACP-OMe
Boc-Phe-His-AHCH-Leu-DACH-OMe
BOC-Phe-Nle-AHCP-Ile-DAMH-OMe
POA-His-AHCP-Ile-DAMH-OMe
3-phenylpropionyl-His-AHCP-Ile-DAMH-OMe
(2-benzyl-4-phenylbutyryl)-His-AHCP-Ile-DAMH-OMe
(2-benzyl-4-phenylbutyryl)-His-DACP-Ile-Sta-OMe
as well as the (other) corresponding 3R,4S-derivatives of these compounds.

EXAMPLE 4

Analogously to Example 3, 4R-(BOC-Phe-His-Sta-Ile-amino)-5S-isobutyl-pyrrolidone, m.p. 105° (decomposition) is obtained by hydrogenolysis of 4R-[BOC-Phe-(imi-BOM-His)-Sta-Ile-amino]-5S-isobutyl-pyrrolidone [m.p. 120°–123° (decomposition); obtainable by cyclization of methyl 3S-CBZ-amino-4R-BOC-amino-6-methylpentanoate hydrochloride with 1N sodium hydroxide solution at 20° to give 4R-CBZ-amino-5S-isobutyl-pyrrolidone (m.p. 119°), hydrogenolysis to give 4R-amino-5S-isobutyl-pyrrolidone (oil; Rf 0.13 on silica gel, methylene chloride/methanol 9:1), condensation with BOC-Ile-OH/DCCI/HOBt to give 4R-BOC-Ile-amino-5S-isobutyl-pyrrolidone, splitting off the BOC group with HCl/dioxane and condensation with BOC-Phe-(imi-BOM-His)-Sta-OH (m.p. 156°–158°)].

The following compounds are obtained analogously by hydrogenolysis of the corresponding (imi-BOM-His) derivatives or CBZ derivatives:
4S-(BOC-Phe-His-Sta-Ile-amino)-5S-isobutyl-pyrrolidone
4R-(BOC-Phe-His-Sta-amino)-5S-isobutyl-pyrrolidone, m.p. 122°–123°

4S-(BOC-Phe-His-Sta-amino)-5S-isobutyl-pyrrolidone
4S-(BOC-Phe-His-AHPP-amino)-5S-isobutyl-pyrrolidone
4S-(BOC-Phe-His-AHCP-amino)-5S-isobutyl-pyrrolidone
4S-(BOC-Phe-His-AHCH-amino)-5S-isobutyl-pyrrolidone
4S-(BOC-Phe-His-DAMH-amino)-5S-isobutyl-pyrrolidone
4S-(BOC-Phe-His-DAPP-amino)-5S-isobutyl-pyrrolidone
4S-(BOC-Phe-His-DACP-amino)-5S-isobutyl-pyrrolidone
4S-(BOC-Phe-His-DACH-amino)-5S-isobutyl-pyrrolidone, m.p. 205°–208°
4S-(BOC-Phe-His-AHPP-Ile-amino)-5S-isobutyl-pyrrolidone
4S-(BOC-Phe-His-AHCP-Ile-amino)-5S-isobutyl-pyrrolidone
4S-(BOC-Phe-His-AHCH-Ile-amino)-5S-isobutyl-pyrrolidone
4S-(BOC-Phe-His-DAMH-Ile-amino)-5S-isobutyl-pyrrolidone
4S-(BOC-Phe-His-DAPP-Ile-amino)-5S-isobutyl-pyrrolidone
4S-(BOC-Phe-His-DACP-Ile-amino)-5S-isobutyl-pyrrolidone
4S-(BOC-Phe-His-DACH-Ile-amino)-5S-isobutyl-pyrrolidone
4S-(BOC-Phe-Abu-AHCP-amino)-5S-isobutyl-pyrrolidone
4S-(BOC-Phe-His-AHCP-amino)-5S-isobutyl-pyrrolidone
4S-(BOC-Phe-Leu-AHCP-amino)-5S-isobutyl-pyrrolidone
4S-(BOC-Phe-Nle-AHCP-amino)-5S-isobutyl-pyrrolidone
4S-[BOC-(N-Me-Phe)-His-AHCP-amino]-5S-isobutyl-pyrrolidone
4S-[(3-phenylpropionyl)-(N-Me-Phe)-His-AHCP-amino]-5S-isobutyl-pyrrolidone
4S-[(2-benzyl-4-phenylbutyryl)-(N-Me-Phe)-His-AHCP-amino]-5S-isobutyl-pyrrolidone
4S-(POA-His-Sta-Ile-amino)-5S-isobutyl-pyrrolidone
4S-[(3-phenylpropionyl)-His-Sta-Ile-amino]-5S-isobutylpyrrolidone
4S-[(4-phenylbutyryl)-His-Sta-Ile-amino]-5S-isobutyl-pyrrolidone
4S-[(2-benzyl-3-phenyl-propionyl)-His-Sta-Ile-amino]-5S-isobutyl-pyrrolidone
4S-[(2-benzyl-4-phenylbutyryl)-His-Sta-Ile-amino]-5S-isobutyl-pyrrolidone
4S-[(2-benzyl-4-phenylbutyryl)-His-AHPP-Ile-amino]-5S-isobutyl-pyrrolidone
4S-[(2-benzyl-4-phenylbutyryl)-His-AHCP-Ile-amino]-5S-isobutyl-pyrrolidone
4S-[(2-benzyl-4-phenylbutyryl)-His-AHCH-Ile-amino]-5S-isobutyl-pyrrolidone
4S-[(2-benzyl-4-phenylbutyryl)-His-DAMH-Ile-amino]-5S-isobutyl-pyrrolidone
4S-[(2-benzyl-4-phenylbutyryl)-His-DAPP-Ile-amino]-5S-isobutyl-pyrrolidone
4S-[(2-benzyl-4-phenylbutyryl)-His-DACP-Ile-amino]-5S-isobutyl-pyrrolidone
4S-[(2-benzyl-4-phenylbutyryl)-His-DACH-Ile-amino-5S-isobutyl-pyrrolidone
4S-(BOC-Phe-His-Sta-Abu-amino)-5S-isobutyl-pyrrolidone
4S-(BOC-Phe-His-Sta-Leu-amino)-5S-isobutyl-pyrrolidone
4S-(BOC-Phe-His-Sta-Met-amino)-5S-isobutyl-pyrrolidone
4S-(BOC-Phe-His-Sta-Nle-amino)-5S-isobutyl-pyrrolidone
4S-(BOC-Phe-His-Sta-Val-amino)-5S-isobutyl-pyrrolidone
4S-[BOC-(N-Me-Phe)-His-Sta-Ile-amino]-5S-isobutyl-pyrrolidone
4S-(BOC-Phe-Dab-Sta-Ile-amino)-5S-isobutyl-pyrrolidone
4S-(BOC-Phe-Lys-Sta-Ile-amino)-5S-isobutyl-pyrrolidone
4S-(BOC-Phe-Orn-Sta-Ile-amino)-5S-isobutyl-pyrrolidone
4S-(BOC-Trp-His-Sta-Ile-amino)-5S-isobutyl-pyrrolidone
4S-(BOC-Tyr-His-Sta-Ile-amino)-5S-isobutyl-pyrrolidone
as well as the 4R, 5S epimers of these compounds.

EXAMPLE 5

70 g of hydroxylamino hydrochloride are added to a solution of 841 mg of methyl 3-oxo-4S-(3S-hydroxy-4S-BOC-L-phenylalanyl-L-histidylamino-6-methyl-heptanoylamino-L-isoleucyl-amino)-6-methylheptanoate and 1.43 g of $Na_2CO_3.10H_2O$ in 5 ml of methanol and 5 ml of water and the mixture is stirred at $20^4$ for 14 hours. The oxime which has precipitated out is filtered off, dried, dissolved in 10 ml of methanol and hydrogenated on 0.5 g of Raney Ni at 20° under 5 bar. The catalyst is filtered off, the filtrate is evaporated and the residue is separated on silica gel (methylene chloride/methanol/acetic acid/water) to give methyl 3S-amino-4S-(3S-hydroxy-4S-BOC-L-phenylalanyl-L-histidylamino-6-methylheptanoylamino-L-isoleucylamino)-6-methyl-heptanoate ("BOC-Phe-His-Sta-Ile-DAMH-OMe"), m.p. 166°–167°; in addition, the 3R-amino epimer is obtained.

EXAMPLE 6

A solution of 841 mg of methyl 3-oxo-4S-(3S-hydroxy-4S-BOC-Phe-His-NH-6-methylheptanoyl-Ile-amino)-6-methylheptanoate and 250 mg of benzylamine in 10 ml of ethanol is stirred at 20° C. for 16 hours. After addition of 0.5 g of Pd-on-charcoal (5%), the resulting Schiff's base is hydrogenated at 20° C. under 1 bar for 8 hours. After 1 equivalent of $H_2$ has been taken up, the catalyst is filtered off and the filtrate is evaporated, the resulting diastereomer mixture of the two 3-benzylamino compounds is dissolved in 5 ml of 50% ethanol, 0.5 g of palladium hydroxide-on-charcoal is added and hydrogenation is carried out again at 20° C. under 1 bar for 16 hours. After filtration, evaporation and fractional recrystallization from ethanol, BOC-Phe-His-Sta-Ile-DAMH-OMe, m.p. 166°–167°, and the corresponding 3R-amino epimer are obtained.

The following compounds are obtained analogously from the corresponding 3-oxo compounds:
BOC-Phe-His-Sta-Abu-DAMH-OMe
BOC-Phe-His-Sta-Ala-DAMH-OMe
BOC-Phe-His-Sta-Leu-DAMH-OMe, m.p. 161°–162°
BOC-Phe-His-Sta-Met-DAMH-OMe
BOC-Phe-His-Sta-Nle-DAMH-OMe
BOC-Phe-His-Sta-Val-DAMH-OMe
BOC-Phe-His-Sta-Abu-DAPP-OMe
BOC-Phe-His-Sta-Ala-DAPP-OMe BOC-Phe-His-Sta-Ile-DAPP-OMe
BOC-Phe-His-Sta-Leu-DAPP-OMe
BOC-Phe-His-Sta-Met-DAPP-OMe
BOC-Phe-His-Sta-Nle-DAPP-OMe
BOC-Phe-His-Sta-Val-DAPP-OMe
BOC-Phe-His-Sta-Abu-DACP-OMe
BOC-Phe-His-Sta-Ala-DACP-OMe
BOC-Phe-His-Sta-Ile-DACP-OMe
BOC-Phe-His-Sta-Leu-DACP-OMe
BOC-Phe-His-Sta-Met-DACP-OMe
BOC-Phe-His-Sta-Nle-DACP-OMe
BOC-Phe-His-Sta-Val-DACP-OMe as well as the corresponding 3R, 4S epimers, such as BOC-Phe-His-Sta-Leu-(3R,4S)-DAPP-OMe, m.p. 203°.

EXAMPLE 7

1.01 g of N-methylmorpholine are added to a solution of 1.92 g of 4S-amino-5S-isobutyl-pyrrolidone hydrochloride in 50 ml of methylene chloride. 5.2 g of BOC-Phe-NLe-Sta-OH, 1.35 g of HOBt and a solution of 2.06 g of DCCI in 50 ml of methylene chloride are added, the mixture is stirred at 4° for 14 hours, the dicyclohexylurea which has precipitated out is filtered off and the filtrate is evaporated. The residue is taken up in ethyl acetate and the mixture is washed with 1N HCl and 1N sodium hydroxide solution and dried over magnesium sulfate. Purification by chromatography on silica gel with methylene chloride/methanol gives 4S-(BOC-Phe-Nle-Sta-amino)-5S-isobutyl-pyrrolidone. m.p. 131°.

The following corresponding peptide-carboxylic acids are obtained analogously:

4S-(BOC-Phe-Abu-Sta-Ile-amino)-5S-isobutyl-pyrrolidone
4S-(BOC-Phe-Asn-Sta-Ile-amino)-5S-isobutyl-pyrrolidone
4S-(BOC-Phe-Gln-Sta-Ile-amino)-5S-isobutyl-pyrrolidone
4S-(BOC-Phe-Leu-Sta-Ile-amino)-5S-isobutyl-pyrrolidone
4S-(BOC-Phe-Nle-Sta-Ile-amino)-5S-isobutyl-pyrrolidone
4S-[BOC-Phe-(N-imi-methyl-His)-Sta-Ile-amino]-5S-isobutyl-pyrrolidone.

EXAMPLE 8

A solution of 1 g of BOC-Phe-His-Sta-Ile-DAMH-OMe in 20 ml of 4N HCl in dioxane is stirred at 20° for 30 minutes and then evaporated. Phe-His-Sta-Ile-DAMH-OMe is obtained.

The corresponding peptide esters are obtained analogously by splitting the corresponding N-BOC derivatives.

EXAMPLE 9

In analogy to Example 3, there are obtained by hydrogenolysis of the corresponding CBZ or of the corresponding CBZ-imi-BOM-His or of the corresponding imi-BOM-His derivatives:

BOC-Phe-NLe-DACP-Sta-OMe, m.p. 86°–88°
BOC-Phe-His-DACH-Ile-(3R,4S)-DAMH-OMe, m.p. 117°14 122°
4S-(BOC-Phe-His-Sta-amino)-5S-isobutyl-pyrrolidone
4S-(BOC-Phe-His-AHCP-amino)-5S-isobutyl-pyrrolidone
4S-(BOC-Phe-His-AHCH-amino)-5S-isobutyl-pyrrolidone
4S-(BOC-Phe-His-DAMH-amino)-5S-isobutyl-pyrrolidone
4S-(BOC-Phe-His-DAPP-amino)-5S-isobutyl-pyrrolidone
4S-(BOC-Phe-His-DACP-amino)-5S-isobutyl-pyrrolidone
4S-(BOC-Phe-His-DACH-amino)-5S-isobutyl-pyrrolidone
BOC-Phe-(imi-Me-His)-DACP-Ile-(3R,4S)-Sta-OMe, m.p. 157° (dec.)
4R-(BOC-Phe-His-Sta-amino)-5S-benzyl-pyrrolidone, m.p. 133°–135°
4R-(BOC-Phe-His-Sta-amino)-5S-isobutyl-pyrrolidone
4R-(BOC-Phe-His-AHPP-amino)-5S-isobutyl-pyrrolidone
4R-(BOC-Phe-His-AHCP-amino)-5S-isobutyl-pyrrolidone, m.p. 145°–148°
4R-(BOC-Phe-His-AHCH-amino)-5S-isobutyl-pyrrolidone
4R-(BOC-Phe-His-DAMH-amino)-5S-isobutyl-pyrrolidone
4R-(BOC-Phe-His-DAPP-amino)-5S-isobutyl-pyrrolidone
4R-(BOC-Phe-His-DACP-amino)-5S-isobutyl-pyrrolidone
4R-(BOC-Phe-His-DACH-amino)-5S-isobutyl-pyrrolidone
4R-[(2-benzyl-4-phenylbutyryl)-His-AHCP-amino]-5S-isobutyl-pyrrolidone
4S-[(2-benzyl-4-phenylbutyryl)-His-AHCP-amino]-5S-isobutyl-pyrrolidone, m.p. 147°–149°
4S-[(4-phenylbutyryl)-His-AHCP-amino]-5S-isobutyl-pyrrolidone, m.p. 223° (dec.)
BOC-Phe-His-AHCP-Ile-(3R,4S)-DAMH-OMe, m.p. 185°–187°
4R-(BOC-Phe-His-AHCP-Ile-amino)-5S-isobutyl-pyrrolidone, m.p. 140°–142°
4S-[(4,4-diphenylbutyryl)-His-AHCP-amino]-5S-isobutyl-pyrrolidone, m.p. 123°–125°
4S-[(3,3-diphenylpropionyl)-His-AHCP-amino]-5S-isobutyl-pyrrolidone, m.p. 221°–224°
4S-(POA-His-AHCP-amino)-5S-isobutyl-pyrrolidone, m.p. 110° (dec.)
4S-(benzoyl-His-AHCP-amino)-5S-isobutyl-pyrrolidone, m.p. 238° (dec.)
BOC-Phe-His-AHCP-(3R,4S)-DAMH-OMe, m.p. 127°–129°
BOC-Phe-His-AHCP-DAMH-OH, m.p. 135° (dec.)
4S-[2-(2-phenylethyl)-4-phenylpropionyl-His-AHCP-amino]-5S-isobutyl-pyrrolidone, m.p. 166°–168°
4S-[(2-benzyl-3-phenylpropionyl)-His-AHCP-amino]-5S-isobutyl-pyrrolidone, m.p. 154°–157°
4R-[BOC-(N-Me-Phe)-His-AHCP-amino]-5S-isobutyl-pyrrolidone, m.p. 210°–215°
4R-(BOC-Tic-His-AHCP-amino)-5S-isobutyl-pyrrolidone, m.p. 165°
(2-benzyl-4-phenylbutyryl)-His-AHCP-Ile-(3R,4S)-DAMH-OMe, m.p. 194° (dec.)
(2-benzyl-4-phenylbutyryl)-His-AHCP-Ile-(3R,4S)-DAMH-OH, formiate, m.p. 207° (dec.)
(2-benzyl-4-phenylbutyryl)-Ala-AHCP-Ile-(3R,4S)-DAMH-OMe, m.p. 195° (dec.)
(2-benzyl-4-phenylbutyryl)-His-AHCP-Sta-NH₂, m.p. 108°–109°
4R-(BOC-Phe-Orn-AHCP-amino)-5S-isobutyl-pyrrolidone
4R-(BOC-Phe-Lys-AHCP-amino)-5S-isobutyl-pyrrolidone
4R-(BOC-Phe-Dab-AHCP-amino)-5S-isobutyl-pyrrolidone 4R-(2-benzyl-4-phenylbutyryl-Orn-AHCP-amino)-5S-isobutyl-pyrrolidone
4R-(2-benzyl-4-phenylbutyryl-Lys-AHCP-amino)-5S-isobutyl-pyrrolidone
4R-(2-benzyl-4-phenylbutyryl-Dab-AHCP-amino)-5S-isobutyl-pyrrolidone.

EXAMPLE 10

An analogy to Example 7, there are obtained:
4R-(BOC-Phe-Ala-AHCP-amino)-5S-isobutyl-pyrrolidone
4R-(2-benzyl-4-phenylbutyryl-Ala-AHCP-amino)-5S-isobutyl-pyrrolidone.

The following examples relate to pharmaceutical formulations.

EXAMPLE A

Injection bottles

A solution of 100 g of BOC-Phe-His-Sta-Ile-DAMH-OMe and 5 g of disodium hydrogen phosphate in 3 l of doubly distilled water is brought to pH 6.5 with 2N hydrochloric acid, sterile-filtered, bottled in injection bottles, lyophilized under sterile conditions and sealed under sterile conditions. Each injection bottle contains 500 mg of active compound.

EXAMPLE B

Suppositories

A mixture of 500 g of BOC-Phe-His-DACP-Ile-Sta-OMe is melted with 100 g of soya lecithin and 1,400 g of cacao butter, poured into molds and allowed to cool. Each suppository contains 500 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A peptide of the formula

X—Z—W—E—W'—Y wherein
X is H, $R^1$—O—$C_mH_{2m}$—CO—, $R^1$—$C_mH_{2m}$—O—CO—, $R^1$—$C_mH_{2m}$—CO—, $R^1$—$SO_2$—, ($R^1$—$C_mH_{2m}$)—L($R^1$—$C_pH_{2p}$)—$C_rH_{2r}$—CO—, H—(NHCH$_2$CH$_2$)$_m$—NH—CH$_2$CO— or 9-fluorenyl-$C_mH_{2m}$—O—CO, Z is 0 to 4 amino acid radicals bonded together in peptide form, each being independently Abu, Ada, Ala, Arg, Asn, Bia, Dab, Gln, Gly, His, N(im)-alkyl-His, Ile, Leu, tert.-Leu, Lys, Met, Nbg, Nle, Orn, Phe, Pro, Ser, Thr, Tic, Trp, Tyr or Val, W and W' are each independently —NR$^2$—CHR$^3$—CHR$^4$—(CHR$^5$)$_n$—CO—, E is 0 to 2 amino acid radicals bonded to one another in peptide form, each being independently Abu, Ala, Ile, Leu, Met, Nle or Val, Y is —O—$C_tH_{2t}$—R$^6$, —NH—$C_tH_{2t}$—R$^6$ of NA$_2$, or W'—Y is also

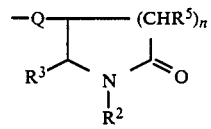

$R^1$ and $R^3$ are each independently A, Ar, Ar-alkyl, cycloalkyl of 3–7C atoms, cycloalkyl substituted by alkyl, alkoxy or Hal, cycloalkyl-alkyl of 4–11C atoms, bicycloalkyl or tricyclo-alkyl each of 7–14C atoms, or bicycloalkyl-alkyl or tricycloalkyl-alkyl of 8–18C atoms, $R^2$, $R^5$, and $R^6$ are each independently H or A, $R^4$ is OH or NH$_2$, L is CH or N, m, p, r and t are each independently 0, 1, 2, 3, 4 or 5, n is 1 or 2, Q is O or NH, Ar is phenyl, naphthyl or phenyl substituted by A, AO, Hal, CF$_3$, OH or NH$_2$, Hal is F, Cl Br or I, and A is alkyl of 1–8C atoms, wherein, one or more —NH—CO— groups can be replaced by —N(alkyl)—CO—, wherein in W and W', one radical R$^4$ is OH and the other is NH$_2$, and wherein the radicals R$^2$, R$^3$, R$^5$, A and Hal and the parameters n can be identical or different, or a pharmaceutically acceptable salt thereof.

2. A compound of claim 1, wherein A is of 1–4C atoms.

3. A compound of claim 1, wherein R$^1$ is A.

4. A compound of claim 1, wherein R$^2$, R$^5$ and R$^6$ are each H or CH$_3$.

5. A compound of claim 1 wherein R$^3$ is A.

6. A compound of claim 1 wherein m, p, r and t are independently 0, 1 or 2 and n is 1.

7. A compound of claim 1 wherein X is H, POA, BOC, CBZ, acetyl, propionyl, butyryl, isobutyryl, cyclopentylcarbonyl, cyclohexylcarbonyl, benzoyl, phenylacetyl, 2- or 3-phenylpropionyl, 4-phenylbutyryl, 2-benzyl-4-phenylbutyryl, 2- or 3-o-, -m- or -p-fluorophenylpropionyl, 2- or 3-o-, -m- or -p-chlorophenylpropionyl cyclohexylacetyl or 2- or 3-cyclohexylpropionyl, BOC is tert.-butoxycarbonyl, CBZ is benzyloxycarbonyl and POA is phenoxyacetyl.

8. A compound of claim 1 wherein Z is His, Phe-His, Pro-Phe-His or His-Pro-Phe-His.

9. A compound of claim 1 wherein Z is Abu, Ada, Asn, Bia, Gln, N-(imi)-alkyl-His, Leu, Nle, Phe, Trp, Tyr, Abu-His, Ada-His, Ala-His, Ala-Phe, Arg-His, Asn-His, Bia-His, Dab-His, Gly-His, His-His, Ile-His, Leu-His, tert.-Leu-His, Lys-His, Met-His, Nbg-His, Nle-His, (N-Me-His)-His, (N-Me-Phe)-His, Orn-His, Phe-Abu, Phe-Ada, Phe-Ala, Phe-Arg, Phe-Asn, Phe-Bia, Phe-Dab, Phe-Gln, Phe-Gly, Phe-(N-im-alkyl-His), Phe-Ile, Phe-Leu, Phe-tert.-Leu, Phe-Lys, Phe-Met, Phe-Nbg, Phe-Nle, Phe-(N-Me-His), Phe-(N-Me-Phe), Phe-Orn, Phe-Phe, Phe-Pro, Phe-Ser, Phe-Thr, Phe-Tic, Phe-Trp, Phe-Tyr, Phe-Val, Pro-His, Ser-His, Thr-His, Tic-His, Trp-His, Tyr-His, Val-His, Ada-Phe-His, Pro-Ala-His, Pro-Ala-Phe, Pro-Phe-Ala, Pro-Phe-Phe, His-Pro-Ala-His, His-Pro-Ala-Phe, His-Pro-Phe-Ala, His-Pro-Phe-Phe, furthermore Pro-Abu-His, Pro-Ada-His, Pro-Arg-His, Pro-Asn-His, Pro-Bia-His, Pro-Dab-His, Pro-Gly-His, Pro-His-His, Pro-Ile-His, Pro-Leu- His, Pro-tert.-Leu-His, Pro-Lys-His, Pro-Met-His, Pro-Nbg-His, Pro-Nle-His, Pro-(N-Me-His)-His, Pro-(N-Me-Phe)-His, Pro-Orn-His, Pro-Phe-Abu, Pro-Phe-Ada, Pro-Phe-Arg, Pro-Phe-Asn, Pro-Phe-Bia, Pro-Phe-Dab, Pro-Phe-Gln, Pro-Phe-Gly, Pro-Phe-(N-im-alkyl-His), Pro-Phe-Ile, Pro-Phe-Leu, Pro-Phe-tert.-Leu, Pro-Phe-Lys, Pro-Phe-Met, Pro-Phe-Nbg, Pro-Phe-Nle, Pro-Phe-(N-Me-His), Pro-Phe-(N-Me-Phe), Pro-Phe-Orn, Pro-Phe-Pro, Pro-Phe-Ser, Pro-Phe-Thr, Pro-Phe-Tic, Pro-Phe-Trp, Pro-Phe-Tyr, Pro-Phe-Val, Pro-Pro-His, Pro-Ser-His, Pro-Thr-His, Pro-Tic-His, Pro-Trp-His, Pro-Tyr-His, Pro-Val-His, His-Pro-Abu-His, His-Pro-Ada-His, His-Pro-Arg-His, His-Pro-Asn-His, His-Pro-Bia-His, His-Pro-Dab-His, His-Pro-Gly-His, His-Pro-His-His, His-Pro-Ile-His, His-Pro-Leu-His, His-Pro-tert.-Leu-His, His-Pro-Lys-His, His-Pro-Met-His, His-Pro-Nbg-His, His-Pro-Nle-His, His-Pro-(N-Me-His)-His, His-Pro-(N-Me-Phe)-His, His-Pro-Orn-His, His-Pro-Phe-Abu, His-Pro-Phe-Ada, His-Pro-Phe-Arg, His-Pro-Phe-Asn, His-Pro-Phe-Bia, His-Pro-Phe-Dab, His-Pro-Phe-Gln, His-Pro-Phe-Gly, His-Pro-Phe(N-im-alkyl-His), His-Pro-Phe-Ile, His-Pro-Phe-Leu, His-Pro-Phe-tert.-Leu, His-Pro-Phe-Lys, His-Pro-Phe-Met, His-PrO-Phe-Nbg, His-Pro-Phe-Nle, His-Pro-Phe-(N-Me-His), His-Pro-Phe-(N-Me-Phe), His-Pro-Phe-Orn, His-Pro-Phe-Pro, His-Pro-Phe-Ser, His-Pro-Phe-Thr, His-Pro-Phe-Tic, His-Pro-Phe-Trp, His-Pro-Phe-Tyr, His-Pro-Phe-Val, His-Pro-Pro-His, His-Pro-Ser-His, His-Pro-Thr-His, His-Pro-Tic-His, His-Pro-Trp-His, His-Pro-Tyr-His or His-Pro-Val-His.

10. A compound of claim 1 wherein one of the groups W and W' is —NH—CH(isobutyl)-CHOH-CH$_2$—CO—, —NH—CH(benzyl)—CHOH—CH$_2$—CO—, —NH—CH(cyclohexylmethyL)-CHOH—CH$_2$—CO— or —NH—CH(CH$_2$CH$_2$-cyclohexyl)-CHOH—CH$_2$—CO and the other of the groups W and W' is —NH—CH(isobutyl)-CH(NH$_2$)—CH$_2$—CO—, —NH—CH(benzyl)-CH(NH$_2$)—CH$_2$—CO—, —NH—CH(cyclohexylmethyl)-CH(NH$_2$)—CH$_2$—CO— or —NH—CH(CH$_2$CH$_2$-cyclohexyl)-CH(NH$_2$)—CH$_2$—CO—.

11. A compound of claim 1 wherein
X is H, phenoxyacetyl, tert.-butoxycarbonyl, 4-phenylbutyryl, 2-benzyl-4-phenylbutyryl on benzyloxycarbonyl,
Z is absent or is His, Phe-His, Pro-Phe-His or His-Pro-Phe-His,
W is (a) —NH—CHR$^3$—CHOH—CH$_2$—CO— or (b) —NH—CHR$^3$—CH(NH$_2$)—CH$_2$—CO—,
E is absent or is Ile or Leu,
W' is (a) —NH—CHR$^3$—CH(NH$^2$)—CH$_2$—CO— or (b) —NH—CHR$^3$—CHOH—CH$_2$—CO—,
R$^3$ is isobutyl, benzyl or cyclohexylmethyl and
Y is OH or OMe, or
W'—Y is also

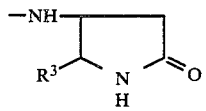

12. A compound of claim 1 wherein
X is H, phenoxyacetyl, tert.-butoxycarbonyl 4-phenylbutyryl, 2-benzyl-4-phenylbutyryl or benzyloxycarbonyl,
Z is absent or is His, Phe-His, Pro-Phe-His or His-Pro-Phe-His,
W is —NH—CHR$^3$—CHOH—CH$_2$—CO—,
E is absent or is Ile or Leu,
W' is —NH—CHR$^3$—CH(NH$_2$)—CH$_2$—CO—,
R is isobutyl, benzyl or cyclohexylmethyl and
Y is OH or OMe.

13. A compound of claim 1 wherein
X is H, phenoxyacetyl, tert.-butoxycarbonyl, 4-phenylbutyryl, 2-benzyl-4-phenylbutyryl or benzyloxycarbonyl,
Z is absent or is His, Phe-His, Pro-Phe-His or His-Pro-Phe-His,
W is —NH—CHR$^3$—CH(NH$_2$)—CH$_2$—CO—,
E is absent or is Ile or Leu,
W' is —NH—CHR$^3$—CHOH—CH$_2$—CO—,
R$^3$ is isobutyl, benzyl or cyclohexylmethyl and
Y is OH or OMe.

14. A compound of claim 1 wherein
X is H, phenoxyacetyl, tert.-butoxycarbonyl, 4-phenylbutyryl, 2-benzyl-4-pehnylbutyryl or benzyloxycarbonyl,
Z is absent or is His, Phe-His, Pro-Phe-His or His-Pro-Phe-His,
W is —NH—CHR$^3$—CHR$^4$—CH$_2$—CO—,
E is absent or is Ile or Leu,
W'—Y is

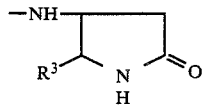

and
R$^3$ is isobutyl, benzyl or cyclohexylmethyl.

15. A compound of claim 1 wherein
X is H or tert.-butoxycarbonyl,
Z is Phe-His,
W is (a) Sta or (b) —NH—CH(isobutyl)-CH(NH$_2$)—CH$_2$—CO—, —NH—CH(cyclohexylmethyl)-CH(NH$_2$)—CH$_2$—CO—, or —NH—CH(benzyl)-CH(NH$_2$)—CH$_2$—CO—,
E is absent or is Ile or Leu,
W' is (a) —NH—CH(isobutyl)-CH(NH$_2$)—CH$_2$—CO—, —NH—CH(cyclohexylmethyl)-CH(NH$_2$)—CH$_2$—CO—, —NH—CH(benzyl)-CH$_2$(NH$_2$)—CH$_2$—CO—, or (b) Sta and
Y is OH or OMe, or
W'—Y is also

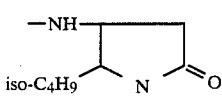

wherein Sta is —NH—CH(isobutyl)-CHOH—CH$_2$—CO—.

16. A compound of claim 1 wherein
X is tert.-butoxycarbonyl,
Z is Phe-His,
W is (a) Sta or (b) —NH—CH(isobutyl)-CH(NH$_2$)—CH$_2$—CO—, —NH—CH(cyclohexylmethyl)-CH(NH$_2$)—CH$_2$—CO—, —NH—CH(benzyl)-CH(NH$_2$)—CH$_2$—CO—,
E is absent or is Ile or Leu, W' is (a) —NH—CH(isobutyl)-CH(NH$_2$)—CH$_2$—CO—, —NH—CH(cyclohexylmethyl)-CH(NH$_2$)—CH$_2$—CO—, —NH—CH(benzyl)-CH(NH$_2$)—CH$_2$—CO—, or (b) Sta and
Y is OH or OMe, or
W'—Y is also

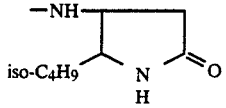

wherein Sta is —NH—CH(isobutyl)-CHOH—CH$_2$—CO—.

17. (a) Methyl 3-amino-4-(BOC-Phe-His-Sta-Ile-amino)-6-methyl-heptanoate;
(b) Methyl 3-amino-4-(BOC-Phe-His-Sta-Leu-amino)-5-phenyl-pentanoate;
(c) N-(3-Amino-4-(BOC-Phe-His-amino)-5-cyclohexylpentanoyl)-isoleucyl-statine methyl ester; or
(d) N-(3-Amino-4-(BOC-Phe-Nle-amino)-5-cyclohexylpentanoyl)-isoleucyl-statine
each a compound of claim 1.

18. A pharmaceutical composition comprising a compound of claim 1, and a compatible carrier.
19. A composition of claim 18, wherein the amount of said compound is 500 mg to 5 g.
20. A method of treating or preventing hypertension comprising administering a compound of claim 1.
21. A method of treating or preventing hyperaldosteronism comprising administering a compound of claim 1.
22. A method of treating or preventing a disease contributed to by renin, comprising administering a compound of claim 1.
23. A compound of the formula

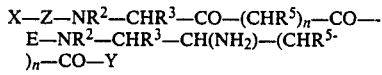

wherein X, Z, R$^2$, R$^3$, R$^5$, n, E and Y are as in claim 1.

24. A compound of the formula

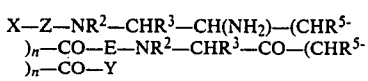

wherein X, Z, R$^2$, R$^3$, R$^5$, n, E and Y are as in claim 1.

* * * * *